United States Patent [19]

Hunt et al.

[11] 4,374,851

[45] Feb. 22, 1983

[54] METHOD OF CONTROLLING PARASITIC TICKS

[75] Inventors: LaWanda M. Hunt, Kerrville, Tex.; Malcolm J. Thompson, Baltimore; William E. Robbins, Silver Spring, both of Md.

[73] Assignee: The United States of America as represented by the Secretary of Agriculture, Washington, D.C.

[21] Appl. No.: 326,995

[22] Filed: Dec. 3, 1981

Related U.S. Application Data

[62] Division of Ser. No. 134,008, Mar. 26, 1980, Pat. No. 4,310,547.

[51] Int. Cl.³ ............................................. A01N 43/08
[52] U.S. Cl. .............................. 424/285; 424/DIG. 8
[58] Field of Search .......................... 424/285, DIG. 8

[56] References Cited

U.S. PATENT DOCUMENTS

| | | | |
|---|---|---|---|
| 2,030,093 | 2/1936 | Bousquet et al. | 424/325 |
| 3,226,293 | 12/1965 | Ursprung | 424/325 |
| 4,036,987 | 7/1977 | Thompson et al. | 424/325 |
| 4,073,939 | 2/1978 | Thompson et al. | 424/320 |
| 4,230,726 | 10/1980 | Fisher et al. | 424/325 |

FOREIGN PATENT DOCUMENTS

| | | | |
|---|---|---|---|
| 259671 | 5/1963 | Australia | 424/325 |
| 673277 | 10/1963 | Canada | 424/325 |

OTHER PUBLICATIONS

King; Chem. Eval. as Insecticides and Repellents at Orlando, Fla. (1954), pp. 11 & 244.
Ishizuka et al.; C.A., vol. 76 (1972), #81003x.

Primary Examiner—Allen J. Robinson
Attorney, Agent, or Firm—M. Howard Silverstein; William E. Scott; David G. McConnell

[57] ABSTRACT

Certain amines are highly effective in controlling parasitic ticks.

2 Claims, No Drawings

METHOD OF CONTROLLING PARASITIC TICKS

This is a division, of application Ser. No. 134,008, filed Mar. 26, 1980 now U.S. Pat. No. 4,310,547.

BACKGROUND OF THE INVENTION

1. Field of the Invention

This invention relates to the control of parasitic ticks and more specifically to the control of ticks that affect man and domestic animals with certain straight and branched-chain amines.

2. Description of the Art

Currently, the number of pesticides available for tick control is very limited even though there are some pesticides registered with the Environmental Protection Agency for use as tick control agents. Of the registered pesticides, only two are for use on lactating dairy cattle. A disadvantage of the pesticides currently registered for tick control is the short period that they are effective after being applied to the host animal. The six compounds that are available for control of ticks on beef cattle and horses break down rapidly on the hair coat of the animals and provide only short term residual protection even when used as a spray or a dip for whole body treatment. Consequently, reinfestation by ticks occurs within a few days of treatment. This means that the animals would have to be treated on a regularly scheduled basis in order to provide adequate and continuous protection. However, this is not only expensive because of the cost of labor and materials, but it may also be very impractical, if not impossible, because of a lack of available manpower.

Some of the compounds of this invention are also useful in the control of nematodes and other helminths U.S. Pat. Nos. 4,036,987 and 4,073,939, and in the control of parasitic mites.

SUMMARY OF THE INVENTION

An object of this invention is to provide new chemicals that are useful in the control of parasitic ticks through systemic activity.

Another object is to provide chemicals that are lethal to ticks at a critical stage in their life cycle.

A further object is to provide compounds that control ticks at concentrations below those required for presently available chemicals.

A still further object is to provide compounds that will control ticks safely and economically and that have low vertebrate toxicity and are not toxic or harmful to the host animal.

In general, according to this invention certain straight and branched-chain amines having chain lengths of from about 8 to 18 carbon atoms are found to be highly effective for controlling parasitic ticks. When administered to a host animal the compounds act systemically and are ingested by ticks which engorge themselves on the host animal. Dosage rates are designed to be non-toxic to the host animal yet lethal to the tick and effective in reducing the number of progeny produced by the ticks. A convenient method of administration is to inject a solution of the compound into the host animal subcutaneously. However, other methods may also be used. The compound can be incorporated into feed or feed additives or into salt blocks, or it can be implanted in a capsule underneath the skin of the animal. In the latter method, the implant could be easily removed when the animal reaches the market. In fact, any method of administration which results in the compound being absorbed into the host animal's system is satisfactory for the purposes of this invention. Compounds found to be useful for the purposes of this invention have the following general formulas:

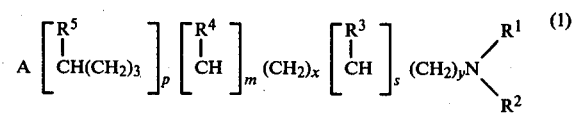

wherein A is selected from the group $CH_3$, $CH_2\!\!=\!\!CH$, or $(CH_3)_2N$ and when A is $CH_2\!\!=\!\!CH$ or $(CH_3)_2N$, each of p, m, x and s are zero; $R^1$ and $R^2$ are individually H, alkyl from 1 to 12 carbon atoms,

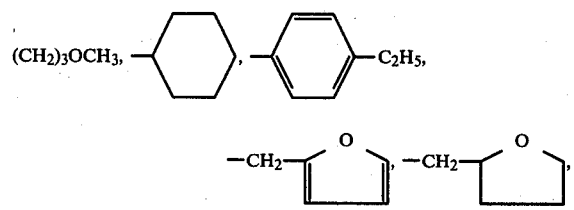

or taken together with the N is

$R^3$, $R^4$, and $R^5$ are individually lower alkyl, p, m and s are individually zero or the integer 1, x is zero or the integer 3, and y is integer from 2 to 13; and

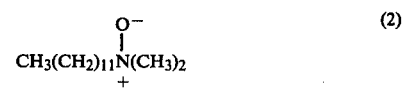

and $$CH_3(CH_2)_{11}S(CH_2)_3NHCH_3 \qquad (3)$$

DESCRIPTION OF THE INVENTION

In the years 1973 to 1975 the average annual loss caused to domestic animals by ticks was estimated to be $442 million for beef cattle, $40 million for dairy cattle, $17 million for sheep and goats, $10 million for horses, and $100 million for pets. In 1971 alone 11.7 million pounds of insecticide were used solely for tick control on beef and dairy cattle, which represented 79% of the total insecticide applied to all classes of livestock for pest control that year.

Animal parasitic ticks cause serious damage and/or death to both man and domestic animals. Although only relatively few of the more than 700 species of ticks in the world are important to man and his domestic animals, those few are responsible for the transmission of a large variety of diseases which may cause paralysis, serious physical damage and/or death. In addition, tick infestations per se cause weight loss, anemia, irritation, loss of fitness and paralysis in livestock, and in horses cause "water belly". Infestation of one species of tick frequently not only results in "gauch" ear (damaged ears) but the wounds are often so extensive that the animals are predisposed to screwworm attack, thus endangering the ongoing eradication program for screwworm control in the United States and Mexico. Other species of ticks transmit a number of important diseases including Rocky Mountain spotted fever, Q fever, tularemia, Colorado tick fever, Powassan encephalitis, human babesiosis, and relapsing fever and equine Piroplasmosis. The damage and losses because of disease transmission and the effect on human health are essentially inestimable.

As noted above, the pesticides that are currently available for tick control are applied to the host animal externally and thus, act by direct contact. Pesticides that act systemically against ticks rather than by contact would, because of the number and diversity of possible methods of formulation and administration, the advantageous over those which act by direct contact. They can be used in implants or incorporated into feed additives or salt blocks and thus be effective for longer periods of time and simpler and less costly to use.

The difficulty in finding active compounds is attested to by the limited number of pesticides available for controlling ticks. In the last 20 years, the USDA Laboratory at Kerrville, Tex. has tested some 1500 experimental compounds for systemic activity against ticks without discovering a single compound that could be used as a systemic pesticide for tick control at a practical dosage level. Consequently, it was very surprising and quite unexpected when we found that a number of N-substituted alkyl amines of this invention displayed very high systemic activity against ticks.

The amines were tested in vivo for systemic activity against adult lone star ticks, *Ambylomma americanum*, using guinea pigs as the host animal. Guinea pigs were "close-clipped" around the midsection and 2 capsule cages were attached with contact cement and tape. The pigs were then infested with 16 starved adult lone star ticks, 4 males and 4 females per capsule. The guinea pigs were weighed and the quantity of test compound to be administered was determined. The test chemicals were administered subcutaneously as diethylsuccinate solutions in a volume of less than 0.5 ml on 3 alternate days, beginning 6 days after the ticks were placed in the capsules. All chemicals were initially tested at 30 mg/kg and compounds that were either highly effective against ticks or toxic to the host animal were retested at lower dosage rates. The engorged females were removed as they detached from the host and held in an environmental chamber. The weight of the egg masses produced was recorded, the eggs were incubated to determine the percent hatch and the number of viable larvae produced. The percent control was calculated by determining the decrease in the number of progeny produced by ticks fed on guinea pigs administered the amines as compared to ticks fed on untreated guinea pigs. The reduction in progeny by N-substituted amines resulted from the cumulative effects of one or more of the following: a decrease in the number of eggs produced; a reduction in the percentage of the eggs that hatched; and a decrease in the number of newly hatched larvae that survived. As shown in Table I, a surprising number of the straight chain amines of this invention exhibited systemic activity for tick control by reducing the number of progeny by 34% or more in lone star ticks fed on guinea pigs administered the amines subcutaneously at 30 mg/kg for 3 alternate days. Seven of the 31 compounds in Table I caused a 74% or greater reduction of progeny and the three most active chemicals, compounds 11, 25, and 29, reduced progeny by 99, 97, and 90%, respectively. Compounds 11 and 25 were retested at 5 mg/kg subcutaneously for 3 alternate days and even at this low dosage rate these two chemicals reduced progeny production in lone star ticks in 92 and 100% respectively.

The compounds were prepared in 60-80% yield according to the general method of reaction of the appropriate acid with thionyl chloride to give the respective acid chloride which when reacted with the appropriate amine or ammonia yielded the amide which was reduced to the long chain or branched-chain amine with lithium aluminum hydride in tetrahydrofuran. N-methyl derivatives of secondary amines were prepared by adding formalin to a solution of the amine in 90% formic acid and refluxing the mixture for eight hours. The amines could be in most cases purified via formation of the amine hydrochloride and by reconversion to the free amine or by column chromatography.

The outline of synthesis according to general known method is as follows:

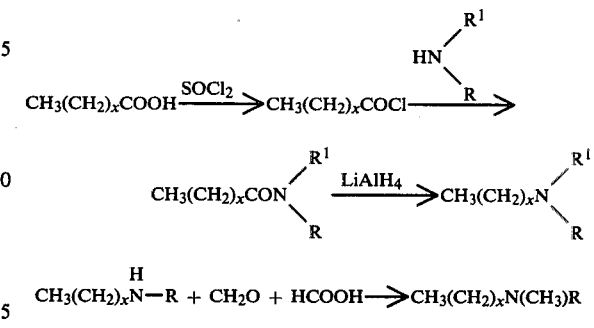

The typical preparation of N,N-dimethyldodecanamine illustrated in U.S. Pat. No. 4,036,987 is also applicable to the amines of this invention. A further typical preparation is illustrated by the following detailed example of the synthesis of

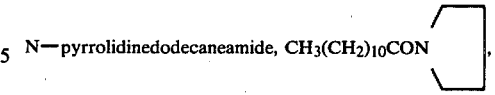

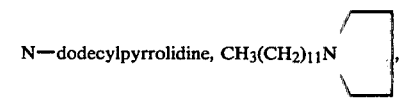

and N-Isoamyl-N-methyldodecanamine, $CH_3(CH_2)_{11}N(CH_3)(CH_2)_2CH(CH_3)_2$.

A mixture of 20 g of lauric acid (dodecanoic acid), 100 ml of dry benzene and 14.3 g (8.9 ml) of thionyl chloride was gently refluxed for about 16 hrs. The solvent and excess thionyl chloride were removed to yield 21.9 g of crude acid chloride. To a mechanically stirred solution of the crude acid chloride in 100 ml of benzene chilled to 10° C. was added 17.9 g (21 ml) of pyrrolidine in 100 ml of benzene. The reaction mixture was stirred for 2 hrs at room temperature, and then filtered. The filtrate was concentrated to dryness under vacuum to give 25.5 g of crude N-pyrrolidine-dodecanamide, >95% pure. Trace amounts of pyrrolidine and pyrrolidine hydrochloride were removed by partitioning the crude amide between diethyl ether and a dilute solution of hydrochloric acid then followed by water. The ether phase dried over sodium sulfate and concentrated to dryness under vacuum yielded 25 g of >99% N-pyrrolidine dodecanamide, $N_D^{20}1.4758$.

Crude N-pyrrolidineodecanamide (15 g) in 100 ml of dry tetrahydrofuran (THF) was added dropwise to a refluxing solution (mechanically stirred) of 2.3 g of solid lithium aluminum hydride in 200 ml of THF, and the solution was refluxed for about 16 hrs, after which, two drops of ethyl acetate were added to determine if an excess of lithium aluminum hydride was still present. The reaction mixture was chilled to 10° C., 25 ml of water added with caution and then 25 g of sodium hydroxide in 35 ml of water was added. After standing for about 2 hrs with occasional stirring and shaking, a gelatinous mass formed and separated from the THF phase. The THF phase was separated and the residue rinsed with additional THF. The THF phases were combined and concentrated nearly to dryness under vacuum. The liquid amine was dissolved into hexane and the hexane solution was washed with dilute solution of sodium hydroxide, water, then dried over sodium hydroxide pellets. The hexane solution (ca 250 ml) was treated with a slight excess of a 6N solution of hydrogen chloride in isopropanol to precipitate out amine hydrochloride which was collected by filtration. The amine hydrochloride was treated with 3 N sodium hydroxide solution and the amine extracted into hexane. The hexane phase was washed with water, and then dried over sodium hydroxide pellets. Removal of the hexane under vacuum gave 14 g of N-pyrrolidinedodecanamine, $N_D^{20}1.4605$.

To 30 g of N-isoamyldodecanamine in 100 ml of formic acid was added 30 ml of formalin (40% formaldehyde) and the reaction mixture was refluxed for 8 hrs. Most of the solvent was removed under vacuum and the remaining material was made alkaline with 3 N sodium hydroxide solution and the amine extracted into hexane. The hexane phase was washed with water, and then dried over sodium hydroxide pellets. Removal of the hexane under vacuum gave 28 g of N-isoamyl-N-methyldodecanamine, $N_D^{20}1,4507$.

TABLE I

| Number | Compound Formula | Reduction of Progeny % |
|---|---|---|
| 1 | CH$_3$CH(CH$_2$)$_3$CH(CH$_2$)$_2$N(CH$_3$)$_2$ (with CH$_3$, CH$_3$ branches) | 76 |
| 2 | CH$_3$CH(CH$_2$)$_3$CH(CH$_2$)$_3$CH(CH$_2$)$_2$N(CH$_3$)$_2$ (with CH$_3$, CH$_3$, CH$_3$ branches) | 39 |
| 3 | CH$_3$(CH$_2$)$_9$N(CH$_3$)$_2$ | 39 |
| 4 | CH$_3$(CH$_2$)$_{11}$N(CH$_3$)$_2$ | 46 |
| 5 | CH$_3$(CH$_2$)$_{13}$N(CH$_3$)$_2$ | 39 |
| 6 | CH$_3$(CH$_2$)$_9$NHCH$_3$ | 83 |
| 7 | CH$_3$(CH$_2$)$_{10}$NHCH$_3$ | 45 |
| 8 | CH$_3$(CH$_2$)$_{11}$NHC$_3$H$_7$ | 38 |
| 9 | CH$_3$(CH$_2$)$_{11}$NHCH$_3$ | 42 |
| 10 | CH$_3$(CH$_2$)$_{11}$NHCH(CH$_3$)$_2$ | 39 |
| 11 | CH$_3$(CH$_2$)$_{11}$N(CH$_3$)(CH$_2$)$_2$CH(CH$_3$)$_2$ | 99 |
| 12 | (CH$_3$)$_2$N(CH$_2$)$_{10}$N(CH$_3$)$_2$ | 48 |
| 13 | (CH$_3$)$_2$N(CH$_2$)$_{12}$N(CH$_3$)$_2$ | 64 |
| 14 | CH$_2$=CH(CH$_2$)$_9$N(CH$_3$)$_2$ | 50 |
| 15 | CH$_3$(CH$_2$)$_{11}$NH$_2$ | 34 |
| 16 | [CH$_3$(CH$_2$)$_{11}$]$_2$NH | 74 |
| 17 | [CH$_3$(CH$_2$)$_{11}$]$_2$NCH$_3$ | 62 |
| 18 | [CH$_3$(CH$_2$)$_{11}$]$_3$N | 53 |
| 19 | CH$_3$(CH$_2$)$_9$NH(CH$_2$)$_3$OCH$_3$ | 38 |
| 20 | CH$_3$(CH$_2$)$_{11}$NH(CH$_2$)$_3$OCH$_3$ | 72 |
| 21 | CH$_3$(CH$_2$)$_{11}$N(CH$_3$)$_2$ (N-oxide, O$^-$ / +) | 74 |
| 22 | CH$_3$(CH$_2$)$_{11}$S(CH$_2$)$_3$NHCH$_3$ | 48 |
| 23 | CH$_3$(CH$_2$)$_8$N(pyrrolidinyl) | 40 |
| 24 | CH$_3$(CH$_2$)$_{10}$N(pyrrolidinyl) | 52 |
| 25 | CH$_3$(CH$_2$)$_{11}$N(pyrrolidinyl) | 97 |
| 26 | CH$_3$(CH$_2$)$_{12}$N(pyrrolidinyl) | 44 |
| 27 | CH$_3$(CH$_2$)$_{11}$NH—cyclohexyl | 46 |
| 28 | CH$_3$(CH$_2$)$_{11}$NH—C$_6$H$_4$—C$_2$H$_5$ | 35 |
| 29 | CH$_3$(CH$_2$)$_{10}$NHCH$_2$—(2,3-dihydrofuranyl) | 90 |
| 30 | CH$_3$(CH$_2$)$_9$NHCH$_2$—(2,3-dihydrofuranyl) | 48 |
| 31 | CH$_3$(CH$_2$)$_{13}$NHCH$_2$—(2,3-dihydrofuranyl) | 60 |

We claim:

1. A method of controlling parasitic ticks which attack animals comprising administering to said animal in need of treatment a systemically effective amount against said ticks of a compound of the formula CH$_3$(CH$_2$)$_y$NH-A wherein y is an integer from 9 to 13 and A is

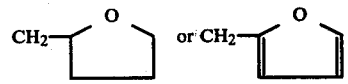

2. The method of claim 1 in which the compound is

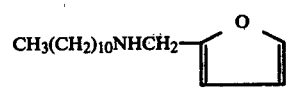

* * * * *